(12) United States Patent
Azuma et al.

(10) Patent No.: US 6,342,531 B1
(45) Date of Patent: Jan. 29, 2002

(54) PHARMACEUTICAL COMPOSITION CONTAINING A CYSTEINE PROTEASE INHIBITOR FOR PROPHYLAXIS AND THERAPY OF BRAIN TISSUE IMPAIRMENT

(75) Inventors: Mitsuyoshi Azuma, Nishinomiya; Yukuo Yoshida, Kobe; Yuji Sakamoto, Kobe; Jun Inoue, Kobe, all of (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/646,529

(22) PCT Filed: Mar. 17, 1999

(86) PCT No.: PCT/JP99/01335

§ 371 Date: Sep. 19, 2000

§ 102(e) Date: Sep. 19, 2000

(87) PCT Pub. No.: WO99/48522

PCT Pub. Date: Sep. 30, 1999

(30) Foreign Application Priority Data

Mar. 20, 1998 (JP) .......................................... 10-072280

(51) Int. Cl.[7] .............................................. A61K 31/18
(52) U.S. Cl. ....................................... 514/601; 514/605
(58) Field of Search ................................. 514/601, 605

(56) References Cited

FOREIGN PATENT DOCUMENTS

| EP | 0 771 565 | 5/1997 |
|---|---|---|
| JP | 771565 A2 * | 5/1997 |
| WO | 92 11850 A | 7/1992 |

OTHER PUBLICATIONS

K. Lee et al. "Inhibition of proteolysis protects hippocampal neurons from ischemia", Proc. Natl. Acad. Sci., vol. 88, pp. 7233–7237, Aug. 1991.

A. Rami et al., "Protective effects of calpain inhibitors against neuronal damage caused by cytotoxic hypoxia in vitro and ischemia in vivo", Brain Research, 609, pp. 67–70, 1993.

S. Inoue et al., "Cellular Detoxification of Tripeptidyl Aldehydes by an Aldo–Keto Reductase", The Journal of Biological Chemistry, vol. 268, No. 8, pp. 5894–5898, Mar. 15, 1993.

Seung–Chyul Hong et al., "Neuroprotection with a Calpain Inhibitor in a Model of Focal Cerebral Ischemia", Stroke, vol. 25, No. 3, pp. 663–669, Mar. 1994.

* cited by examiner

*Primary Examiner*—Dwayne C. Jones
(74) *Attorney, Agent, or Firm*—Wenderoth, Lind & Ponack, L.L.P.

(57) ABSTRACT

A pharmaceutical composition for the prophylaxis and therapy of brain tissue impairment, which contains, as an active ingredient, a compound of the following formula (I)

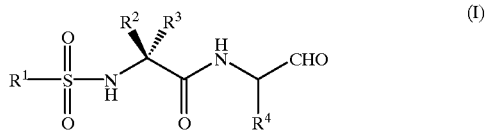

wherein $R^1$ represents an alkyl group having 1–4 carbon atoms or an aryl group having 6–10 carbon atoms which is optionally substituted; $R^2$ and $R^3$ may be the same or different and each represents hydrogen or an alkyl group having 1–4 carbon atoms or $R^2$ and $R^3$ may jointly form a ring having 3–7 carbon atoms; and $R^4$ represents a lower alkyl group which is optionally substituted by aryl, cycloalkyl, or aromatic heterocyclic residue, or a pharmaceutically acceptable salt thereof.

9 Claims, 2 Drawing Sheets

PHARMACEUTICAL COMPOSITION CONTAINING A CYSTEINE PROTEASE INHIBITOR FOR PROPHYLAXIS AND THERAPY OF BRAIN TISSUE IMPAIRMENT

This application is a 371 of PCT/JP99/01335 filed Mar. 17, 1999.

TECHNICAL FIELD

The present invention relates to a prophylactic and therapeutic drug for brain tissue impairment.

BACKGROUND ART

The brain discharges a multi-pronged function including regulation of autonomic nervous system, control of the motion, understanding of the senses, and high-order mental activities such as thinking. When the cerebral blood flow is compromised, the uptake of glucose and oxygen which are essential to the brain function ceases and the brain is no longer able to maintain its homeostasis, with the result that the workings of the brain are seriously handicapped.

Brain tissue impairment results from insufficiency of cerebral blood flow due to various factors or as the result of a complicated interaction of systemic factors such as cardiopathy. Furthermore, the brain tissue is impaired not only by encephalothlipsis secondary to brain trauma, cerebral edema, brain tumor, etc. but also by decreases in cerebral blood flow due to systemic events involving a marked depression of blood pressure such as massive hemorrhage, myocardial infarction, administration of a hypotensive drug, and arrhythmia. The disease caused by such impairment of the brain tissue includes, but is not limited to, cerebral vasospasm, cerebral thrombosis, cerebral infarction, cerebral embolism, intracerebral hemorrhage, subarachnoid hemorrhage, hypertensive encephalopathy, transient ischemic attack, multi-infarct dementia, cerebral arteriosclerosis, and Huntington's disease.

The current pharmacotherapy of brain tissue impairment includes administration of cerebral vasodilators such as cinnarizine, cyclandelate, and pentoxifylline; cerebral metabolism activator such as meclofenoxate hydrochloride, thioctic acid, and GABA; anticoagulants such as heparin sodium; thrombolytic drugs such as urokinase; and platelet aggregation inhibitors such as aspirin and dipyridamole. However, none of those drugs are sufficiently effective; hence the problems remain unsolved.

As recently reported, leupeptin having calpain-inhibitory activity protects neurons against damage by cerebral ischemia [Lee K. S., Frank S., Vanderklish, P., Arai A., Lynch G., Proc. Natl. Acad. Sci., 88, 7233–7237 (1991), Rami A., Krieglstein J., Brain Res., 609, 67–70 (1993), WO92/11850]. However, in those reported studies, the drug is directly administered into the animal cerebral ventricle in consideration of the inability of leupeptin to cross the blood-brain barrier. That is to say, the technology cannot realistically be applied to man. It is disclosed in WO92/11850 that, administered intraperitoneally, certain compounds such as calpain inhibitor I were found to protect neurons from excitotoxic factors. However, calpain inhibitor I is reportedly cytotoxic [Inoue S., Sharma R. C., Schimke R. T., Simoni R. D., J. Biological Chem., 268 (8), 5894–5898 (1993)] and cannot be safely used in man. It has recently been reported that, administered intravenously, the calpain inhibitor Cbz-Val-Phe-H inhibited cytopathy due to cerebral ischemia in rats [Hong S. C., Goto Y., Lanzino G., Soleau S., Kassell N. F., Lee K. S., Stroke, 25 (3), 663–669 (1994)] but its action is not sufficiently strong and, therefore, the drug has not been clinically applied as yet.

The present invention has for its object provision of a prophylactic and therapeutic drug for brain tissue impairment, which has overcome the above-mentioned disadvantages, and of a method for prophylaxis and therapy of such impairment.

DISCLOSURE OF THE INVENTION

The inventors of the present invention endeavored to develop a prophylactic and therapeutic drug for brain tissue impairment, which would cross the blood-brain barrier with ease and be safe to use, and discovered that a compound of the following formula (I)

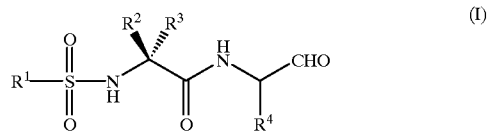

wherein $R^1$ represents an alkyl group having 1–4 carbon atoms or an aryl group having 6–10 carbon atoms which is optionally substituted; $R^2$ and $R^3$ may be the same or different and each represents hydrogen or an alkyl group having 1–4 carbon atoms or $R^2$ and $R^3$ may jointly form a ring. having 3–7 carbon atoms; $R^4$ represents a lower alkyl group which is optionally substituted by aryl, cycloalkyl, or aromatic heterocyclic residue, and a pharmaceutically acceptable salt thereof exhibit remarkable prophylactic or therapeutic efficacy against brain tissue impairment. The present invention has been developed on the basis of the above finding.

In the context of the present invention, brain tissue impairment includes not only impairment of brain tissues associated with cerebral ischemia or cerebral hemorrhage but also secondary impairment of brain tissue due to encephalothlipsis caused by brain trauma, cerebral edema, brain tumor, etc. and impairment of brain tissue associated with circulatory insufficiency of the brain due to systemic events involving a marked depression of blood pressure such as massive hemorrhage, myocardial infarction, administration of a hypotensive drug, arrhythmia, and so forth.

Figure 1:
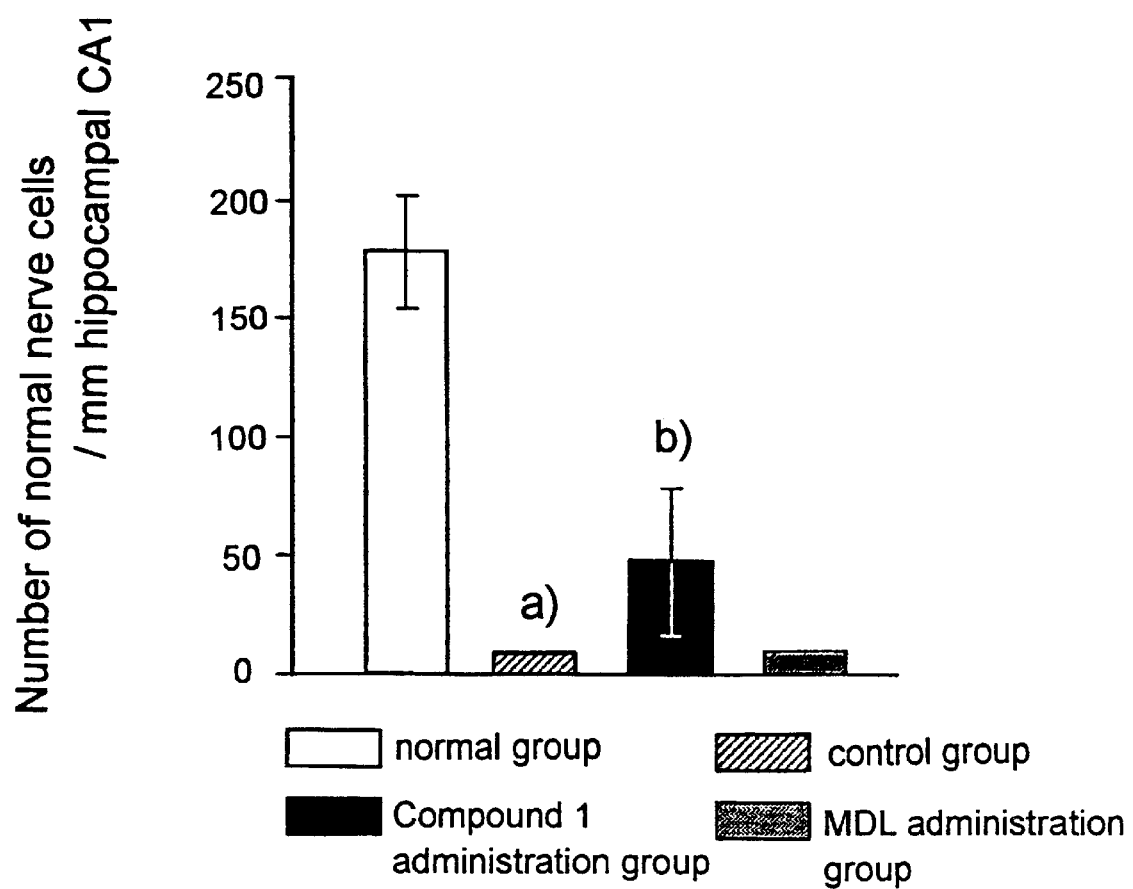
FIG. 1 is a diagrammatic representation of the effect on cytopathy in the hippocampal CA1 region of gerbils. The ordinate represents the number of normal nerve cells in hippocampal CA1 region. In the diagram, a) denotes a significant difference (p<0.01) from the normal group by Student's t-test; b) denotes a significant difference (p<0.05) from the control group by Student's t-test.

The compound of formula (I) for use in present invention and a pharmaceutically acceptable salt thereof are known compounds disclosed in Japanese Patent Unexamined Publication No. 43464/1997 (EP0771565) and can be produced typically by the processes described therein.

Referring to formula (I), when the amino acid moieties exist as optical isomers, they are L-isomers unless otherwise indicated.

Referring further to formula (I), the linear or branched $C_1$–$C_4$ alkyl group mentioned for $R^1$ includes methyl, ethyl, propyl, isopropyl, butyl, isobutyl, sec-butyl, tert-butyl and the like. Of these, methyl is preferred.

The $C_6$–$C_{10}$ aryl group for $R^1$ includes phenyl, naphthyl, indenyl, azulenyl, and so forth. Preferred are phenyl and naphthyl.

The substituent group which may be present on the aryl group includes, for example, halogen (e.g., fluorine, chlorine, etc.), linear or branched $C_1$–$C_5$ alkyl (e.g., methyl, ethyl, propyl, isopropyl, butyl, isobutyl, sec-butyl, tert-butyl, pentyl, isopentyl, neopentyl, tert-pentyl and the like), trifluoromethyl, linear or branched $C_1$–$C_5$ alkoxy (e.g., methoxy, ethoxy, propoxy, isopropoxy, butoxy, isobutoxy, sec-butoxy, tert-butoxy, pentoxy, isopentoxy, neopentoxy, tert-pentoxy and the like), hydroxy, $C_2$–$C_5$ acyloxy (e.g., acetoxy, propionyloxy, butyryloxy, isobutyryloxy, valeryloxy and the like), carboxyl, and $C_2$–$C_5$ acyl (e.g., acetyl, propionyl, butyryl, isobutyryl, valeryl, isovaleryl, pivaroyl and the like). Preferred are halogen and $C_1$–$C_5$ alkyl. The more preferred are fluorine, chlorine, and methyl.

Preferred examples of the optionally substituted $C_6$–$C_{10}$ aryl group for $R^1$ are 4-fluorophenyl, 4-chlorophenyl, p-tolyl, and 2-naphthyl.

The linear or branched $C_1$–$C_4$ alkyl group mentioned for $R^2$ and $R^3$ includes methyl, ethyl, propyl, isopropyl, butyl, isobutyl, sec-butyl, tert-butyl and the like. Preferred are propyl, isopropyl, and tert-butyl. The more preferred is isopropyl.

Referring to $R^2$ and $R^3$, one of them is preferably hydrogen and the other is propyl, isopropyl, isobutyl, or tert-butyl. More preferably, $R^2$ is propyl, isopropyl, isobutyl, or tert-butyl and $R^3$ is hydrogen. Still more preferably, $R^2$ is isopropyl and $R^3$ is hydrogen.

The $C_3$–$C_7$ ring which may be formed jointly by $R^2$ and $R^3$ includes cyclopropylidene, cyclobutylidene, cyclopentylidene, cyclohexylidene, cycloheptylidene, and so forth. Cyclopentylidene and cyclohexylidene are particularly preferred.

The lower alkyl group mentioned for $R^4$ includes linear or branched groups having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, 4-methylpentyl, 1,1-dimethylbutyl, 2,2-dimethylbutyl, 3,3-dimethylbutyl, 2-ethylbutyl and the like. Preferred are methyl and isobutyl. The above-mentioned lower alkyl group may be substituted by the following aryl group, cycloalkyl group, or aromatic heterocyclic residue.

The aryl group includes phenyl, 1-naphthyl, 2-naphthyl, and so forth. Particularly preferred is phenyl.

The cycloalkyl group preferably includes $C_3$–$C_6$ cycloalkyl; for example, cyclopropyl, cyclobutyl, cyclopentyl, cyclohexyl, and so forth. Particularly preferred is cyclohexyl.

The aromatic heterocyclic residue includes heteromonocyclic residues each containing at least one hetero atom selected from the group consisting of oxygen, nitrogen, and sulfur as a ring member and corresponding fused heterocyclic residues. The heteromonocyclic residue includes, but is not limited to, pyrrolyl, furyl, thienyl, oxazolyl, thiazolyl, imidazolyl, pyrazolyl, pyridyl and the like. The fused heterocyclic residue includes, but is not limited to, indolyl, quinolyl, benzothienyl, benzofuryl, indazolyl, quinazolinyl, phthalazinyl, quinoxalinyl and the like. Particularly preferred is indolyl.

Preferred examples of the lower alkyl group which may be substituted by aryl, cycloalkyl or aromatic heterocyclic residue as expressed by $R^4$ are isobutyl, benzyl, cyclohexylmethyl, and indol-3-ylmethyl.

Representative compounds of the formula (I) are

N-(2-naphthalenesulfonyl)-L-valyl-L-leucinal, N-(4-fluorophenylsulfonyl)-L-valyl-L-leucinal, N-(4-chlorophenylsulfonyl)-L-valyl-L-leucinal, N-(4-methylphenylsulfonyl)-L-valyl-L-leucinal, N-(4-fluorophenylsulfonyl)-L-valyl-L-phenylalaninal, N-(2-naphthalenesulfonyl)-L-valyl-L-phenylalaninal, N-(4-chlorophenylsulfonyl)-L-valyl-L-phenylalaninal, N-(4-methylphenylsulfonyl)-L-valyl-L-phenylalaninal, N-(4-chlorophenylsulfonyl)-L-valyl-L-tryptophanal, N-(4-fluorophenylsulfonyl)-L-valyl-L-cyclohexylalaninal, N-(2-naphthalenesulfonyl)-L-valyl-L-cyclohexylalaninal, N-(4-chlorophenylsulfonyl)-L-valyl-L-cyclohexylalaninal, and pharmaceutically acceptable salts thereof.

Particularly preferred are N-(4-fluorophenylsulfonyl)-L-valyl-L-leucinal, and a pharmacutically acceptable salt thereof.

The pharmaceutically acceptable salt of the compound of formula (I) includes salts with inorganic bases; for example, salts with alkali metals such as sodium, potassium, etc., salts with alkaline earth metals such as calcium, magnesium, etc., aluminum salt, ammonium salt, etc.; salts with organic bases such as trimethylamine, pyridine, picoline, ethanolamine, diethanolamine, triethanolamine, dicyclohexylamine, N,N-dibenzylethylenediamine, etc.; salts with inorganic acids such as hydrochloric acid, hydrobromic acid, nitric acid, sulfuric acid, phosphoric acid, etc.; salts with organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; and salts with amino acids such as arginine, lysine, ornithine, aspartic acid, glutamic acid, and so forth.

The prophylactic and therapeutic drug of the present invention can be optionally provided in any dosage form known in the art, that can be manufactured by a known pharmaceutical technology which comprises, for example, mixing or dissolving the active compound with a pharmaceutically acceptable carrier or vehicle. Of such dosage forms, the oral dosage form for use in humans include powders, granules, tablets, capsules, syrups, and other liquid preparations. Powders, granules, tablets and the like can be manufactured using optional pharmaceutically suitable carriers that are suitable for solid preparations, such as excipients (e.g., starch, glucose, fructose, sucrose, lactose, etc.), lubricants (e.g., magnesium stearate, calcium stearate, etc.), disintegrators (e.g., starch, crystalline cellulose, etc.), binders (e.g., starch, gum arabic, etc.), and so forth. Such solid preparation may be optionally coated with a coating agent (e.g., gelatin, sucrose, etc.) or an enteric coating (e.g., hydroxypropylmethylcellulose phthalate, methacrylic copolymers, shellac, etc.), so that the active compound may be released specifically in the bowels. For the manufacture of syrups and other liquids, various additives such as stabilizers (e.g., sodium edetate etc.), suspending agents (e.g., gum arabic, carmellose, etc.), corrigents (e.g., simple syrup, glucose, etc.), perfumes, etc. can be appropriately added. The dosage form for non-oral systemic administration includes injections, suppositories, etc. Injections can be manufactured by using solvents (e.g. water for injection, etc.), stabilizers (e.g., sodium edetate etc.), isotonizing agents (e.g., sodium chloride, glycerol, mannitol, etc.), pH control agents (e.g., hydrochloric acid, citric acid, sodium hydroxide, etc.), suspending agents (e.g., methylcellulose, sodium carboxymethylcellulose, etc.), and other suitable additives. For the manufacture of suppository, a suppository base (e.g., cacao butter, macrogol, etc) and the like may be appropriately used.

The prophylactic and therapeutic drug of the present invention is useful for the prevention and treatment of brain tissue impairment in warm-blooded animals (e.g., human, gerbil, rat, mouse, rabbit, cow, pig, dog, cat, and the like). The disease associated with brain tissue impairment, includes, but is not limited to, cerebral vasospasm, cerebral thrombosis, cerebral infarction, cerebral embolism, intracerebral hemorrhage, subarachnoid hemorrhage, hypertensive encephalopathy, transient ischemic attack, multi-infarct dementia, cerebral arteriosclerosis, and Huntington's disease.

The dosage of the compound of formula (I) or a pharmaceutically acceptable salt thereof according to the present invention is dependent on the target disease, clinical state and other conditions of patients, administration route, and other factors. Generally speaking, the objective effect can be achieved in a general dose of 1–1000 mg, preferably 10–500 mg, for oral administration to adult patient, or generally 0.1–300 mg, preferably 1–150 mg, for parenteral administration to adult patient, once to several times a day.

Unless contrary to the object of the present invention, the prophylactic and therapeutic drug of the present invention can be used in conjunction with other active ingredients. The concomitant ingredients which can be particularly used are cerebral vasodilators such as cinnarizine, cyclandelate, pentoxifylline, etc., cerebral metabolism activator such as meclofenoxate hydrochloride, thioctic acid, GABA, etc.; anticoagulants such as heparin sodium etc.; thrombolytic drugs such as urokinase etc.; platelet aggregation inhibitors such as aspirin, dipyridamole etc.; adrenocorticoids such as hydrocortisone, dexamethasone, etc.; hypertonic solutions such as solutions of glycerol and mannitol; hypotensive drugs such as reserpine, hydralazine hydrochloride, etc.; antibiotics such as semisynthetic penicillins, cephalosporins, etc.; and sedatives/anticonvulsants such as chlorpromazine, diazepam, primidone, carbamazepine, etc.

EXAMPLES

The following examples and test examples are intended to illustrate the present invention in further detail and should by no means be construed as defining the scope of the invention. In the following examples and test examples, Compound 1 means N-(4-fluorophenylsulfonyl)-L-valyl-L-leucinal.

Example 1

| Tablets | |
| --- | --- |
| Compound 1 | 50 mg |
| Lactose | 80 mg |
| Starch | 17 mg |
| Magnesium stearate | 3 mg |
| Crystalline cellulose | 10 mg |

Using the above component materials per tablet, tablets were manufactured by the established pharmaceutical procedure. Where necessary, the tablets may be coated with a conventional enteric coating (e.g., hydroxypropylmethylcellulose phthalate), a sugar coating, or a film (e.g., ethylcellulose).

Example 2

| Capsules | |
| --- | --- |
| Compound 1 | 75 mg |
| Mannitol | 75 mg |
| Starch | 17 mg |
| Calcium stearate | 3 mg |

Using above component materials per capsule were uniformly mixed, granulated by the established pharmaceutical procedure, and filled into hard capsule shells. Where necessary, the granules prior to filling may be coated with a conventional enteric coating (e.g., hydroxypropylmethylcellulose phthalate), a sugar coating, or a film (e.g., ethylcellulose).

Example 3

| Parenteral suspension | |
| --- | --- |
| Compound 1 | 750 mg |
| Sodium carboxymethylcellulose | 500 mg |
| Water for injection | to make 100 ml |

Using the above component materials, a parenteral suspension was manufactured by the established sterile pharmaceutical procedure.

Test Example 1

Effect on Ischemic Disorder of the Brain

Method:

The bilateral common carotid arteries of gerbils (male, body weights 60–80 g) were exposed under ether anesthesia. Then, in a conscious state, the carotid arteries were occluded with aneurysm clips to arrest the blood flow for 10 minutes. Ischemia was confirmed by checking the arrest of retinal blood flow with a blood flow meter (Advance laser flow meter (ALF21N), Advance Co. Ltd.) and observation of ischemic symptoms such as seizure, circling, and ptosis. After removal of the clips, reperfusion was confirmed with the blood flow meter. Five days after reperfusion, the animal was anesthetized with ether and was perfused with saline through the left ventricle for removal of blood and further with 4% formaldehyde for fixation of the brain tissue. The tissue was embedded in paraffin and thin sections were prepared and stained with hematoxylin-eosin in the routine manner. The nerve cells in the hippocampal CA1 region were observed under a light microscope and the normal nerve cells remaining in a 1.0 mm span of the hippocampal CA1 region were counted. Separately, using Apoptosis in situ Detection Kit Wako (Wako Pure Chemical Ind., Ltd.), the apoptosis in the paraffin-embedded brain tissue specimen was detected and using the light microscope, the apoptotic nerve cells per 1.0 mm span of the hippocampal CA1 region were counted.

In the normal group, the common carotid arteries were exposed but no ischemia was introduced. As the test drug, a parenteral suspension prepared as in Example 3 was administered intraperitoneally in a dose of 100 mg Compound 1 per kg body weight 15 minutes before ischemia, immediately after reperfusion, and thereafter once daily (Compound 1 administration group). In the control group and normal group, the vehicle used in Example 3 was similarly administered. As a positive control, Cbz-Val-Phe-H [MDL; S. C. Hong et al., Stroke, 25 (3), 663–669 (1994)], 100 mg/kg body weight, was similarly administered (MDL administration group).

Figure 2:
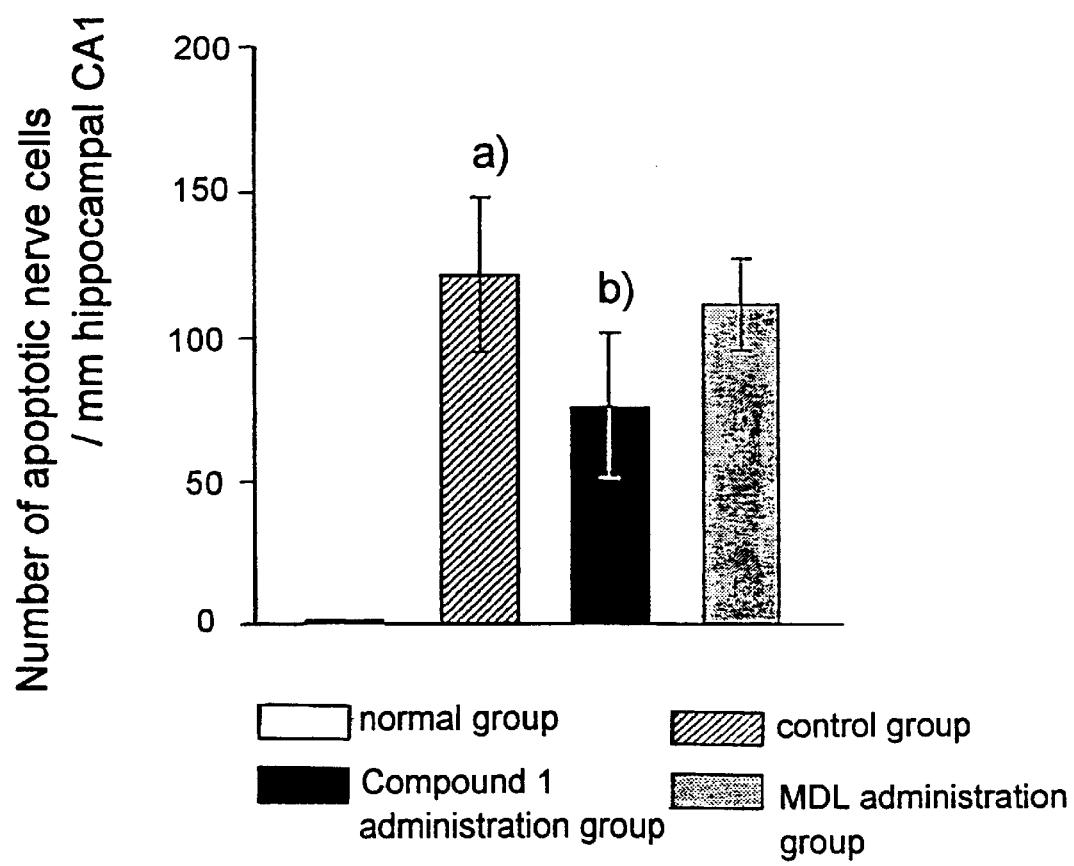
FIG. 2 is a diagrammatic representation of the effect on apoptosis in the hippocampal CA1 region of gerbils. The ordinate represents the number of apoptotic nerve cells in hippocampal CA1 region. In the diagram, a) denotes a significant difference (p<0.01) from the normal group by Student's t-test; b) denotes a significant difference (p<0.01) from the control group by Student's t-test.

Results:

The results are shown in FIGS. 1 and 2.

Ischemia caused a significant decrease in the number of normal nerve cells in the hippocampal CA1 region and a significant increase in the number of apoptotic nerve cells as compared with the normal group. In Compound 1 administration group, the ischemia-induced decrease in the number of normal nerve cells in the hippocampal CA1 region was significantly inhibited and the increase in the number of apoptotic nerve cells was also significantly inhibited. In the MDL administration group, little inhibitory effect was found on the decrease of normal nerve cells or the increase of apoptotic nerve cells in the hippocampus CA1 region.

The above results indicate that, compared with MDL, the active Compound 1 of the present invention passes the blood-brain barrier more efficiently and is useful for the protection of brain tissue against impairment.

Test Example 2

Toxicity Study

Method:

Five-week-old Wister rats (male, body weights 80–105 g) were orally given a 3.3 w/v % suspension of Compound 1 in 0.5 w/v % carboxymethylcellulose in a dose of 1000 mg as Compound 1 per kg body weight. The rats were observed for general condition and behavior immediately after dosing, ¼, ½, 1, 2, 3, and 5 hours after dosing, and thereafter once daily for 14 days. Body weights were recorded before dosing and once daily for 14 days after dosing. Autopsy was performed after sacrifice by exsanguination under ether anesthesia after 14 days and the organs were grossly examined. The control group received 0.5 w/v % carboxymethylcellulose.

Results:

(1) General condition and behavior

Both the control group and Compound 1 administration group showed no change in general condition or in behavior.

(2) Body weight

Between the control group and Compound 1 administration group, no difference was found in body weight gain.

(3) Autopsy findings

Between the control group and Compound 1 administration group, no difference was found in autopsy findings.

INDUSTRIAL APPLICABILITY

The prophylactic and therapeutic drug according to the present invention is useful for the prevention and treatment of diseases arising from brain tissue impairment, such as cerebral vasospasm, cerebral thrombosis, cerebral infarction, cerebral embolism, intracerebral hemorrhage, subarachnoid hemorrhage, hypertensive encephalopathy, transient ischemic attack, multi-infarct dementia, cerebral arteriosclerosis, Huntington's disease, and so forth.

Furthermore, the drug can be used safely in the prophylaxis and therapy of secondary impairment of brain tissue arising from encephalothlipsis associated with brain trauma, cerebral edema, brain tumor, etc. and the brain tissue impairment arising from circulatory insufficiency of the brain due to systemic events involving a marked depression of blood pressure such as massive hemorrhage, myocardial infarction, administration of a hypotensive drug, arrhythmia, and so forth.

The present invention is based on Application No. 72280/1998 filed in Japan, the content of which is incorporated hereinto by reference.

What is claimed is:

1. A method for treatment of brain tissue impairment, which comprises administering, to a warm-blooded animal, an effective amount of a compound of the formula (I):

$$R^1-\overset{O}{\underset{O}{\overset{\|}{S}}}-\underset{H}{N}-\overset{R^2}{\underset{}{\overset{R^3}{C}}}-\overset{O}{\underset{}{C}}-\underset{H}{N}-\overset{H}{\underset{R^4}{C}}-CHO \quad (I)$$

wherein $R^1$ represents an alkyl group having 1 to 4 carbon atoms or an aryl group having 6 to 10 carbon atoms which is optionally substituted; $R^2$ and $R^3$ may be the same or different and each represents hydrogen or an alkyl group having 1 to 4 carbon atoms or $R^2$ and $R^3$ may jointly form a ring having 3 to 7 carbon atoms; and $R^4$ represents a lower alkyl group which is optionally substituted by aryl, cycloalkyl, or aromatic heterocyclic residue, or a pharmaceutically acceptable salt thereof.

2. The method as claimed in claim 1, wherein $R^1$ in the formula (I) is phenyl or naphthyl, which may be substituted by fluorine, chlorine, or methyl.

3. The method as claimed in claim 1, wherein $R^1$ in the formula (I) is a group selected from the group consisting of methyl, 4-fluorophenyl, 4-chlorophenyl, p-tolyl, and 2-naphthyl.

4. The method as claimed in claim 1, wherein, in the formula (I), $R^2$ is propyl, isopropyl, or tert-butyl and $R^3$ is hydrogen.

5. The method as claimed in claim 1, wherein, in the formula (I), $R^2$ is isopropyl and $R^3$ is hydrogen.

6. The method as claimed in claim 1, wherein, in the formula (I), $R^2$ and $R^3$ jointly form cyclopentylidene or cyclohexylidene.

7. The method as claimed in claim 1, wherein, in the formula (I), $R^4$ is a group selected from the group consisting of isobutyl, benzyl, cyclohexylmethyl, and indol-3-ylmethyl.

8. The method as claimed in claim 1, wherein the active ingredient is N-(4-fluorophenylsulfonyl)-L-valyl-L-leucinal or a pharmaceutically acceptable salt thereof.

9. The method as claimed in any of claim 1 to claim 8, wherein the brain tissue impairment is associated with circulatory insufficiency of the brain.

* * * * *